United States Patent [19]

Zilg

[11] Patent Number: 4,645,670

[45] Date of Patent: Feb. 24, 1987

[54] PROCESS FOR THE STABILIZATION OF HEMATIN

[75] Inventor: Harald Zilg, Marburg, Fed. Rep. of Germany

[73] Assignee: Behringwerke Aktiengesellschaft, Fed. Rep. of Germany

[21] Appl. No.: 593,406

[22] Filed: Mar. 26, 1984

[30] Foreign Application Priority Data

Mar. 28, 1983 [DE]  Fed. Rep. of Germany ....... 3311288

[51] Int. Cl.$^4$ .................... A61K 35/14; A61K 31/555
[52] U.S. Cl. ..................................... 424/101; 514/185
[58] Field of Search ................. 424/101, 245; 514/185

[56] References Cited

PUBLICATIONS

Merck Index pp. 669–671, 10th Edition (1983).
"Action des Rayons X sur L'Hemine" by Oliveira et al., Arch. Int. Pharmacodyn, 1961, pp. 236–238.
Chemical Abstracts; vol. 97 (1982) #695h; Godin et al.
Chemical Abstracts; vol. 55 (1961) #19008i; Oliveira et al.
Chemical Abstracts, vol. 51 (1957) #2914i; O'Hagan.
Chemical Abstracts, vol. 55 (1961) #10514g; Little et al.
Chemical Abstracts; vol. 47 (1953) #2816g; Rosenfeld et al.
Chemical Abstracts; vol. 47 (1953) #12447b; Fiser-Herman et al.
Chemical Abstracts; vol. 54 (1960) #22752; Aber et al.
Merck Index; 8th Ed. (1968); pp. 29, 520.

*Primary Examiner*—Leonard Schenkman
*Assistant Examiner*—Joseph A. Lipovsky
*Attorney, Agent, or Firm*—Finnegan, Henderson, Farabow, Garrett & Dunner

[57] ABSTRACT

A process for the stabilization of hematin by means of albumin is described. The resulting product is a medicament with improved properties.

5 Claims, No Drawings

PROCESS FOR THE STABILIZATION OF HEMATIN

The invention relates to a process for the stabilization of hematin in solid or dissolved form. The stabilized hematin can be used as a medicament, preferably in the treatment of certain forms of porphyria.

According to the prior art, hematin infusion solutions which are suitable for use on patients are prepared from the active compound hematin immediately before they are required, certain safety measures, especially in respect of freedom from pyrogens, being maintained; this process cannot be realized in every hospital (C. A. Pierach, Der Internist 22 (1981) 726–732). Furthermore, a technique is also known for preparing a hematin product in lyophilized form with the addition of mannitol; a hematin solution with a certain but unsatisfactory life can be prepared by this route, by reconstitution with a suitable solvent (J. M. Lamon et al., Medicine 58 (3) (1979) 252–269).

Surprisingly, it has now been found that albumin is capable of stabilizing hematin products both in solution and in lyophilized form.

The invention thus relates to a process for the preparation of a stabilized hematin product, which comprises adding albumin to the hematin.

For this purpose, a hematin solution can be mixed with an albumin solution and the mixture can be brought to dryness. However, the hematin and albumin, each in solid form, can also be brought together and, if necessary, mixed. It is also possible to bring together one component in solid form with a solution of the other component and to bring the mixture to dryness.

Hematin as the active compound component of such a product is prepared by processes which are known per se (H. Fischer, Org. Synthesis Collective Volume, J. Wiley ed., New York (1955), 3, 442), starting materials of animal origin, but preferably of human origin, and here in turn preferably "degenerated" conserved blood, being used.

Serum albumin of human origin is used as the stabilizing component, albumin which has undergone heating to 60° C. in the presence of suitable stabilizers in accordance with the European Pharmacopeia or other pharmacopeias preferably being used. However, it is moreover also possible to use other serum albumin products of human origin.

The ratio of hematin to albumin is chosen so that after reconstitution of the dried, preferably lyophilized mixture with a solvent, in particular water, which may contain salts to adjust the isotonicity, the hematin concentration is 0.5 to 10 g/liter, but preferably 2 to 7 g/liter, and the albumin concentration is 2 to 200 g/liter, but preferably 7 to 50 g/liter. A procedure can be followed here in which the hematin is dissolved in an alkaline medium, preferably in the pH range from 9–12, in the presence of a suitable buffer substance, but preferably in the absence of a buffer substance, with addition of sodium hydroxide solution. After a pH value of between 7 and 9, preferably between 7.5 and 8.5, has been established, a human albumin solution can then be added. Thereafter, the salt concentration can be adjusted. A physiological NaCl concentration in the reconstituted end product, using a suitable solvent, is preferably aimed for. The mixture of hematin and albumin is brought to dryness, preferably after the desired volume has been poured into a final container and lyophilized.

However, dry hematin and albumin can also be brought together in solid form before being poured or in the final container, and if necessary mixed.

The advantage of using albumin rather than other stabilizers arises from the course of the decrease in the hematin content as a function of time following reconstitution of the lyophilisate, as summarized in the following table. Hematin was determined photometrically here as bis-pyridine-ferroprotoporphyrin IX complex at a wavelength of 554 nm (K. G. Paul et al., Acta chem. scand. (1953) 7, 1284–1287). The solutions each contained 4 g/liter (=100%) of hematin at the time of preparation, and the stated amounts of stabilizer.

TABLE

Hematin content after storage at 4° C. (starting value at reconstitution = 100%)

| Stabilizer | Time after reconstitution | | | |
|---|---|---|---|---|
| | 6 hours | 24 hours | 72 hours | 90 days |
| Albumin 25 g/liter | 99.0 | 98.7 | 97.6 | 96.2 |
| Glycine 10 g/liter | 89.2 | 81.5 | 77.4 | 79.9 |
| Mannitol 4 g/liter | 96.0 | 83.5 | 79.5 | 79.2 |
| Mannitol 10 g/liter | 97.6 | 86.9 | 79.8 | 79.5 |

As can be seen from the table, albumin particularly prevents the drop in hematin content to be observed in the initial phase with the other stabilizers (the presence of the stabilizers does not influence the photometric determination). Moreover, the position of the absorption maximum is not changed in the presence of albumin during this period, whilst hematin solutions without the addition of a stabilizer and with an addition of glycine or mannitol undergo a hypsochromic shift of 2–3 nm after only 24 hours.

Overall, stabilization with albumin is an advance for practical handling of a hematin product in the hospital, since a longer period is available for reconstitution and use on patients, during which the active compound concentration is maintained. On comparison with a non-stabilized hematin solution, albumin-stabilized hematin proved to be tolerated significantly better in tests for local tolerance (intravenous injection into the blocked ear peripheral vein of rabbits).

Therapeutic use of hematin in certain cases of porphyria is a known method. Hematin acts here in the sense of a negative feed-back control regulating the synthesis of the first enzyme of tetrapyrrole biosynthesis, that is to say the δ-aminolevulinic acid synthetase. Genetically caused deficiencies of certain enzymes of the tetrapyrrole biosynthesis may exist but in the latent state these do not lead to disease symptoms. In such patients, porphyria can be induced by various factors, such as intoxication, stress, fasting conditions and the like, and may extend to a potentially fatal disease by accumulation of toxic porphyrin intermediates. The rapid availability of a hematin product is also a logistics problem for the treating hospital in the case of these relatively rare diseases. A gap is closed here with a stable lyophilized product which can be taken from the emergency store and, after reconstitution, does not need to be subjected to restricting stability considerations during use.

The invention is illustrated by the example below.

EXAMPLE 3 g of hematin are suspended in 200 ml of 0.05 N NaOH at room temperature. During the dissolving operation, the pH is kept at pH 10.5 by further addition of NaOH. After one hour, the undissolved material is centrifuged off and the mixture is filtered. The hematin concentration is adjusted to 12.5 g/liter by addition of water and the pH is adjusted to 9.5 with 0.5 N HCl. 37.5 parts by volume of an albumin solution of 200 g liter are added to 100 parts by volume of hematin solution, NaOH solution accordingly being added if the pH falls below 8.0. An osmolality of 135 mOsm/kg is established by addition of saturated NaCl solution. After sterilization by filtration, infusion bottles are filled with 36 ml of the resulting solution and the solution is lyophilized. 75 ml of a solution of 6 g/liter of NaCl are envisaged as the reconstitution solution. The reconstituted product has a hematin concentration of 4 g/liter and an albumin concentration of 25 g/liter.

I claim:

1. A process for the stabilization of a hematin medicament, which comprises adding human serum albumin to hematin, wherein the weight ratio of hematin to albumin is from 1:25 to 5:1.

2. The process as claimed in claim 1, wherein the weight ratio of hematin to albumin is from 1:25 to 1:1.

3. A hematin medicament comprising hematin and human serum albumin wherein the weight ratio hematin to albumin is from 1:25 to 5:1.

4. A hematin medicament as claimed in claim 3 wherein the weight ratio of hematin to albumin is from 1:25 to 1:1.

5. A hematin medicament as claimed in claim 3 wherein the hematin medicament is in a dry form.

* * * * *